US007709233B2

(12) United States Patent
Kopreski

(10) Patent No.: US 7,709,233 B2
(45) Date of Patent: *May 4, 2010

(54) METHOD ENABLING USE OF EXTRACELLULAR RNA EXTRACTED FROM PLASMA OR SERUM TO DETECT, MONITOR OR EVALUATE CANCER

(75) Inventor: Michael S. Kopreski, Long Valley, NJ (US)

(73) Assignee: OncoMEDx, Inc., Long Valley, NJ (US)

( * ) Notice: Subject to any disclaimer, the term of this patent is extended or adjusted under 35 U.S.C. 154(b) by 519 days.

This patent is subject to a terminal disclaimer.

(21) Appl. No.: 10/684,633

(22) Filed: Oct. 14, 2003

(65) Prior Publication Data

US 2005/0069906 A1    Mar. 31, 2005

Related U.S. Application Data

(63) Continuation of application No. 09/966,515, filed on Sep. 28, 2001, now Pat. No. 6,759,217, which is a continuation-in-part of application No. 09/155,152, filed on Sep. 22, 1998, now Pat. No. 6,329,179.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .................... 435/91.2; 435/6; 435/91.1; 435/91.51; 536/23.1; 536/24.3; 536/24.33; 536/25.3

(58) Field of Classification Search ............... 435/6, 435/91.1, 91.2, 183, 91.51; 436/94; 536/23.1, 536/24.3, 24.33, 25.3
See application file for complete search history.

(56) References Cited

U.S. PATENT DOCUMENTS

| 4,350,156 A | 9/1982 | Malchesky |
| 4,631,130 A | 12/1986 | Watanabe |
| 4,683,195 A | 7/1987 | Mullis et al. |
| 4,699,877 A | 10/1987 | Cline et al. |
| 4,738,927 A | 4/1988 | Taniguchi |
| 4,874,853 A | 10/1989 | Rossi |
| 4,874,858 A | 10/1989 | Magistro |
| 4,999,290 A | 3/1991 | Lee |
| 5,087,617 A | 2/1992 | Smith |
| 5,098,890 A | 3/1992 | Gerwitz et al. |
| 5,124,246 A | 6/1992 | Urdea et al. |
| 5,155,018 A | 10/1992 | Gillespie et al. |
| 5,217,889 A | 6/1993 | Roninson et al. |
| 5,274,087 A | 12/1993 | Barnett et al. |
| 5,300,635 A | 4/1994 | Macfarlane |
| 5,409,818 A | 4/1995 | Davey et al. |
| 5,429,923 A | 7/1995 | Seidman |
| 5,470,724 A | 11/1995 | Ahern |
| 5,506,106 A | 4/1996 | Croce |
| 5,532,220 A | 7/1996 | Lee |
| 5,576,178 A | 11/1996 | Emanuel |
| 6,001,987 A | 12/1999 | Perron |
| 6,051,374 A | 4/2000 | Simons |
| 6,057,105 A | 5/2000 | Hoon |
| 6,329,179 B1 | 12/2001 | Kopreski |
| 6,344,317 B2 | 2/2002 | Urnovitz |
| 6,607,898 B1 | 8/2003 | Kopreski |
| 6,759,217 B2 * | 7/2004 | Kopreski .................. 435/91.2 |
| 6,794,135 B1 | 9/2004 | Kopreski et al. |
| 6,916,634 B2 * | 7/2005 | Kopreski .................. 435/91.2 |
| 6,939,671 B2 * | 9/2005 | Kopreski ...................... 435/6 |
| 2004/0058331 A1 | 3/2004 | Akagi |

FOREIGN PATENT DOCUMENTS

| DE | 3717212 A1 | 12/1988 |
| WO | WO 90/09456 A1 | 8/1990 |
| WO | 97/35589 A | 10/1997 |
| WO | 98/14617 A | 4/1998 |
| WO | 99/67397 | 12/1999 |

OTHER PUBLICATIONS

Bairey et al., Lack of Her-2/neu expression in Hodgkin and non-hodgkin lymphoma. Arch. Pathol. Lab. Med., 126, 574-576, 2002.*
Gilmour et al., Expression of erbB-4/her-4 growth factor receptor isoforms in ovarian cancer. Cancer Research, 61, 2169-2716, 2001.*
Zhou et al., Expression of heterogeneous nuclear ribonucleoprotein A2/B1 in bronchial epithelium of chronic smokers. Clinical Cancer Research, 4, 1631-1640, 1998.*
Zhou et al., Differential expression of the early lung cancer detection marker, heterogeneous nuclear ribonucleoprotein-A2/B1 (hnRNP-A2/B1) in normal breast and neoplastic breast cancer. Breast Cancer Research and Treatment, 66, 217-224, 2001.*
Press et al., Expression of the HER-2/neu proto-oncogene in normal human adult and fetal tissues. Oncogene, 5, 953-962, 1990.*
Revillion et al., Quantification of c-erbB-2 gene expression in breast cancer by competitive RT-PCR. Clinical Chemistry, 43, 2114-2120, 1997.*
Hernández et al., c-myc mRNA expression and genomic alterations in mantle cell lymphomas and other nodal non-Hodgkin's lymphomas. Leukemia, 13, 2087-2093, Dec. 1999.*
Fleischhacker et al., Detection of Amplifiable Messenger RNA in the Serum of Patients with Lung Cancer. Annals of the New York Academy of Sciences, 945, 179-188, 2001.*

(Continued)

*Primary Examiner*—Frank W Lu
(74) *Attorney, Agent, or Firm*—McDonnell Boehnen Hulbert & Berghoff

(57) ABSTRACT

The methods of the invention detect epidermal growth factor RNA, epidermal growth factor receptor RNA, her-2/neu RNA, c-myc RNA, heterogeneous nuclear ribonucleoprotein A2/B1 RNA or any combination thereof in blood plasma, serum, and other bodily fluids. The inventive methods are useful for detection, diagnosis, monitoring, treatment, or evaluation of neoplastic disease.

3 Claims, No Drawings

OTHER PUBLICATIONS

Sueoka et al., Detection of plasma hnRNP B1 mRNA, a new cancer biomarker, in lung cancer patients by quantitative real-time polymerase chain reaction. Lung Cancer, 48, 77-83, 2005.*

Carpenter et al., The roles of heterogeneous nuclear ribonucleoproteins in tumour development and progression. Biochimica et Biophysica Acta, 1765, 85-100, 2006.*

Abravaya et al., "Detection of point mutations with a modified ligase chain reaction (GAP-LCR)," *Nucleic Acids* Research 23:675-682 (1995).

Alkema et al., "Characterization and Chromosamal Localization of the Human Prata-Oncogene BMI-1," *Human Mol Genet* 2:1597-1603 (1993).

Aoki et al., "Liposome-mediated in viva gene transfer on antisense K-ras construct inhibits pancreatic tumor dissemination in the murine peritoneal cavity," *Cancer Research* 55:3810-3816 (1995).

Barz et al., "Characterization of Cellular and Extracellular Plasma Membrane Vesicles from a Non-metastasing Lymphoma (Eb) and Its Metastasing Variant (Esb)," *Biochin Biophys Acta* 814:77-84 (1985).

Bauer et al., "Identification of H-2Kb Binding and Immunogenic Peptides from Human Papillama Virus Tumour Antigens E6 and E7," *Scand J Immunol* 42:317-323 (1995).

Blackburn et al., "Electrochemiluminescence detection for development of immunoassays and DNAprobe assays for clinical diagnostics," *Olin Chem* 37/9:1534-1539 (1991).

Bobo et al., "Diagnosis of chlamydia trachomatis cervical infection by detection of amplified DNA with an enzyme immunoassay;" *J din Micra* 28:1968-1973 (1990).

Bocchia et al., "Specific Binding of Leukemia Oncogene Fusion Peptides to HLA Class I Molecules," *Blood* 85:2680-2684 (1995).

Boom et al., "Rapid and Simple Method for Purification of Nucleic Acids," *J Clin Micro* 28:495-503 (1990).

Boom et al., "Rapid Purification of Hepatitis B Virus DNA from Seruc," *J Clin Micro* 29:180-181 (1991).

Brossart et al., "Detection of residual tumor cells in patients with malignant melanoma responding to immunotherapy," *J Immunotherapy* 15:38-41 (1994).

Buchman et al., "Selective RNA amplification: A novel method using d UMP-containing primers and uracil DNA glycosylase," *PCR Methods Applic* 3:28-31 (1993).

Carr et al., "Circulating Membrane Vesicles in Leukemic Blood," *Cancer Research* 45:5944-5951 (1985).

Cheung et al., "Rapid and Sensitive Method for Detection of Hepatitis C Virus RNA by Using Silica Particles," *J Clin Micro* 32:2593-2597 (1994).

Chirgwin et al., "Isolation of biologically active ribonucleic acid from sources enriched in ribonuclease," *Biochemistry* 18:5294-5299 (1979).

Chomczynski and Mackey, "Modification of the TRI reagent (TM) procedure for isolation of RNA from polysaccharide- and proteaglycan-rich sources," *BioTechniques* 19:942-945 (1995).

Chomczynski and Mackey, "Substitution of chloroform by bromochloropropane in the single-step method of RNA isolation," *Analytical Biochemistry* 225:163-164 (1995).

Chomczynski et al., "Single-step method of RNA isolation by acid guanidinium thiocyanate-phenol-chloroform extraction," *Analytical Biochemistry* 162:156-159 (1987).

Chomczynski, "A reagent for the single-step simultaneous isolation of RNA, DNA and proteins from cell and tissue samples," *Biotech* 15:532-537 (1993).

Chu et al., "Thymidylate synthase binds to c-myc RNA in human colon cancer cells and in vitro," *Mol Cell Biol* 15:179-185 (1995).

Cohen, "Biochemical Therapy: Antisense Compounds," *In: Biologic Teraphy of Cancer (DeVita, Hellman, Rosenberg, eds)* J.B. Lippincott, Ca., Philadelphia (1991) pp. 763-775.

Colomer et al., "erB-2 antisense oligonucleotides inhibit the proliferation of breast carcinoma cells with erb-2 oncogene amplification," *Br J Cancer* 70:819-825 (1994).

Coutlee et al., "Immunodetection of DNA with biotinylated RNA probes: A study of reactivity of a monoclonal antibody to DNA-RNA hybrids," *Analytical Biochemistry* 181:96-105 (1989).

Datta et al., "Sensitive Detection of Occult Breast Cancer by the Reverse-transcriptase Polymerase Chain Reaction," *Journal of Clinical Oncology* 12:475-482 (1994).

Davidova and Shapot, "Liporibonucleoprotein Complex as an Integral Part of Animal Cell Plasma Membranes," *FEBS Lett* 6:349-351 (1970).

DiCesare et al., "A high-sensitivity electrochemiluminescense-based detection system for automated PCR product quantitation," *BioTechniques* 15:152-157 (1993).

Doi et al., "Detection of beta-human chorionic ganadotropin mRNA as a marker for cutaneoud malignant melanoma," *Int J Cancer* 65:454-45-. (1996).

Dosaka et al., "A complex pattern of translational initiation and phosphorylation in L-Myc Proteins," *Oncogene* 6:371-378 (1991).

Edmands et al., "Rapid RT-PCR Amplification from Limited Cell Numbers," *PCR Methods Applic* 3:317-319 (1994).

Feng et al., "The RNA component of human telomerase," *Science* 269:1236-1241 (1995).

Fournie et al., "Recovery of nanogram quantities of DNA from plasma and quantitative measurement using labeling by nick translation," *Analytical Biochemistry* 158:250-256 (1986).

Gerhard et al., "Specific detection of carcinoembryonic antigen-expressing tumor cells in bone marrow aspirates by polymerase chain reaction," *J Clin Oncol* 12:725-729 (1994).

Ghossein et al., "Detection of Circulating Tumor Cells in Patients with Localized and Metastatic Prostatic Carcinoma: Clinical Implications," *Journal of Clinical Oncology* 13:1195-1200 (1995).

Higashiyama et al., "Reduced Motility Related Protein-1 (MRP-1/CD9) Gene Expression as a Factor of Poor Prognosis in Non-small Cell Lung Cancer," *Cancer Research* 55:6040-6044 (1995).

Hoon et al., "Detection of occult melanoma cells in blood with a multiple-marker polymerase chain reaction assay," *J Clin Oncol* 13:2109-2116 (1995).

Hoover et al., "Immunatherapy by Active Specific Immunization: Clinical Applications," *In: Biologic-Therapy of Cancer (DeVita, Hellman, Rosenberg, eds)* J.B. Lippincott, Co., Philadelphia (1991) pp. 670-682.

Imai et al., "Detection of HIV-1 RNA in Heparinized Plasma of HIV-1 Seropositive Individuals," *J Virol Methods* 36:181-184 (1992).

Jrdea et al., "Direct and quantitative detection of HIV-I RNA in human plasma with a branched DNA signal amplification assay," *AIDS* 7(suppl 2):S11-514 (1993).

Juckett and Rosenberg, "Actions of Cis-diamminedichloroplatinum on Cell Surface Nucleic Acids in Cancer Cells as Determined by Cell Electrophoresis Techniques," *Cancer Research* 42:3565-3573 (1982).

Kahn et al., "Rapid and sensitive nonradioactive detection of mutant K-ras genes via enriched PCR amplification," *Oncogene* 6:1079-1083 (1991).

Kamm and Smith, "Nucleic acid concentrations in normal human plasma," *Clinical Chemistry* 18:519-522 (1972).

Karet et al, "Quantification of mRNA in human tissue using fluorescent nested reverse-transcriptase polymerase chain reaction," *Analytical Biochemistry* 220:384-390 (1994).

Katz et al., "Enhanced Reverse Transcriptase-Polymerase Chain Reaction for Prostate Specific Antigen as a Indicator of True Pathologic Stage in Patients with Prostate Cancer," *Cancer* 75:1642-1648 (1995).

Kievits et al., "NASBA(TM) isothermal enzymatic in vitro nucleic acid amplification optimized for the diagnosis of HIV-1 infection," *J Virological Methods* 35:273-286 (1991).

Kim et al., "Specific association of human telomerase activity with immortal cells and cancer," *Science* 266:2011-2015 (1994).

Komeda et al., "Sensitive detection of circulating heptocellular carcinoma cells in peripheral venous load," *Cancer* 75:2214-2219 (1995).

Landgraf et al., "Direct analysis of polymerase chain reaction products using enzyme-linked immunasorbent assay techniques," *Analytical Biochmistry* 198:86-91 (1991).

Landgraf et al., "Quantitative analysis of polymerase chain reaction (PCR) products using primers labeled with biotin and a fluorescent dye," *Analytical Biochemistry* 193:231-235 (1991).

Larson et al., "Radioisotope Conjugates," *In: Biologic Therapy of Cancer (De Vita, Hellman, Rosenberg, eds)* J.B. Lippincott, Co., Philadelphia (1991) pp. 496-511.

Leon et al., "A Comparison of DNA and DNA-binding Protein Levels in Malignant Disease," *Europ J Cancer* 17:533-538 (1981).

Maruyama et al., "Detection of AMLi/ETO fusion transcript as a tool for diagnosing t(8;21) positive acute myelogenous leukemia," *Leukemia* 8:40-45 (1994).

Mesella et al., "Characterization of Vesicles, Containing an Acylated Oligopeptide, Released by Human Colon Adenocarcinoma Cells," *FEBS Lett* 246:25-29 (1989).

McCabe et al., "Minimal Determinant Expressed by a Recombinant Viaccinia Virus Elicits Therapeutic Antitumor Cytolytic T Lumphocyte Responses," *Cancer Research* 55:1741-1747 (1995).

Miller et al., "Detection of minimal residual disease in acute promyelocytic leukemia by a reverse transcription polymerase chain reaction assay for the PML/RAR-alpha fusion mRNA," *Blood* 82:1689-1694 (1993).

Moore et al., "Design of PCR primers that detect only mRNA in the presence of DNA," *Nucleic Acids Research* 18:1921 (1991).

Mori, et al., "Detection of Cancer Micrometastases in Lymph Nodes by Reverse Transcriptase-Polymerase Chain Reaction," *Cancer Research* 55:3417-3420 (1995).

Mountford et al., "Proteolipid Identified by Magnetic Resonance Spectroscopy in Plasma of a Patient with Borderline Ovarian Tumor," *Lancet* i:829-834 (1987).

Nguyen, "Southern blot analysis of polymerase chain reaction products on acrylamide gels," *BioTechniques* 7:238-240 (1989).

Ozcelik et al., "Low Levels of Expression of an Inhibitor of Cyclin-dependent Kinases (CIP1/WAF1) in Primary Breast Carcinomas with p53 Mutations," *Clinical Cancer Research* 1:907-912 (1995).

Patard et al., "Expression of MAGE genes in transitional-cell carcinomas of the urinary bladder," *mt J Cancer* 64:60-64 (1995).

Penno et al., "Expression of CD44 in human lung tumors," *Cancer Research* 54:1381-1387 (1994).

Peoples et al., "Breast and Ovarian Cancer-Specific Cytotoxic T Lymphocytes Recognize the same HER-2/Neu Derived Peptide," *Proc Natl Acad Sci USA* 92:432-436 (1995).

Pfleiderer et al., "Detection of tumor cells in peripheral blood and bone marrow from ewing tumor patients by RT-PCR," *Int J Cancer (Pred. Oncol)* 64:135-139 (1995).

Polushin et al., "Antisense Pro-Drugs: 5'-ester oligodeoxynucleotides," *Nucleic Acids Research* 22:5492-5496 (1994).

Rashtchian, "Amplification of RNA," *PCR Methods Applic* 4:S83-S91 (1994).

Reddi and Holland, "Elevated Serum Ribonuclease in Patients with Pancreatic Cancer," *Proc Nat Acad Sci USA* 73:2308-2310 (1976).

Rieber and Bacalao, "An 'external' RNA removable from mammalian cells by mild proteolysis," *Proc Natl Acad Sci USA* 71:4960-4964 (1974).

Roggenbuck et al., "Human Papillomavirus Type 18 E6 and E6, and E7 Protein Synthesis in Cell Free Translation Systems and Comparison of E6 and E7 in Vitro Translation Products to Proteins Immunoprecipitated from Human Epthelial Cells," *J Viral* 65:5068-72 (1991).

Rosenberg-Nicolson et al., "Nucleoprotein Complexes Released from Lymphoma Nuclei that Contain the abl Oncogene and RNA and DNA Polymerase and RNA Primase Activities," *J Cell Biochem* 50:43-52 (1992).

Rosi et al., "RNA-Lipid Complexes Released from the Plasma Membrane of Human Colon Carcinoma Cells," *Cancer Lett* 39:153-160 (1988).

Saiki et al., "Genetic analysis of amplified DNA with immobilized sequence-specific oligonucleotide probes," *Science* 233:1076-1078 (1989).

Sakakura et al., "Inhibition of gastric cancer cell proliferation by antisense oligonucleotides targeting the messenger RNA encoding proliferating cell nuclear antigen," *Br J Cancer* 70:1060-1066 (1994).

Schlom, "Antibodies in cancer therapy: basic principles of monaclanal antibodies," *In: Biologic Therapy of Cancer, (De Vita, Hellman, Hellman, Rosenberg, eds)* J.B. Lippincott, Co., Philadelphia (1991) pp. 464-481.

Shea et al., "Identification of the Human Prostate Carcinoma Onogene PTI-1 by Rapid Expression Cloning and Differential RNA Display," *Proc Natl Acad Sci USA* 92:6778-6782 (1995).

Skorski et al., "Suppression of philadelphial leukemia cell growth in mice by BORABL antisense oligodeoxynucleotide," *Proc Natl Acad Sci USA* 91:4504-4508 (1994).

Smith et al., "Detection of Melanoma Cells in Peripheral Blood by Means of Reverse Transcriptase and Polymerase Chain Reaction," *Lancet* 338:1227-1229 (1991).

Sooknanan et al., "Detection and direct sequence identification of BCR-ABL mRNA in Ph+ chronic myeloid leukemia," *Experimental Hematology* 21:1718-1724 (1993).

Stock et al., "Value of molecular monitoring during the treatment of chronic myeloid leukemia: A cancer and leukemia group B study," *J Olin Oncology* 15:26-36 (1997).

Stroun et al., "Neoplastic characteristics of the DNA found in the plasma of cancer patients," *Oncology* 46:318-322 (1989).

Taylor and Blak, "Shedding of Plasma Membrane Fragments. Neoplastic and Developmental Importance," *In: The Cell Surface in Development and Cancer, Develop Biol* 3:33-57 Editor: M.S. Steinberg. Plenum Press, New York, London (1985).

Urdea et al., "Branched DNA amplification multimers for the sensitive, direct detection of human hepatitis viruses," *Nucleic Acids Research Symposium Series* 24:197-200 (1991).

Vandamme et al., "Detection of HIV-1 RNA in plasma and serum samples using the NASBA amplification system compared to RNA-PCR," *J Virological Methods* 52:121-132 (1995).

Vitetta et al., "Immunotoxins," *In: Biologic Therapy of Cancer (DeVita, Hellman, Rosenberg, eds)* J.B. Lippincott, Co., Philadelphia (1991) pp. 482-495.

Wang et al., "Quantitation of mRNA by the polymerase chain reaction," *Proc Natl Acad Sci USA* 86:9717-9721 (1989).

Wieczorek et al., "Diagnostic and Prognostic Value of RNA-Proteolipid in Sera of Patients with Malignant Disorders Following Therapy; First Clinical Evaluation of a Novel Tumor Marker," *Cancer Research* 47:6407-6412 (1987).

Wieczorek et al., "Gensondentest Fur RNA-Proteolipid in Serumproben Bei Neoplasie," *Schweiz med Wschr* 119:1342-1343 (1989).

Wieczorek et al., "Isolation and Characterization of an RNA-Proteolipid Complex Associated with the Malignant State in Humans," *Proc Natl Acad Sci USA* 82:3455-3459 (1985).

Wiedmann at al., "Ligase chain reaction (LCR)—overview and applications," *POR Methods Applic* 3:551-564 (1994).

Yanuck et al., "A Mutant P53 Tumor Suppressor Protein is a Target for Peptide-Induced 0DB' Cytotoxic T-Cells," *Cancer Research* 52:3257-3261 (1993).

Office Action, Non-Final Rejection mailed on Nov. 4, 1999 for U.S. Appl. No. 09/155,152.

Office Action, Non-Final Rejection mailed on Apr. 20, 2000 for U.S. Appl. No. 09/155,152.

Office Action, Final Rejection mailed on Oct. 25, 2000 for U.S. Appl. No. 09/155,152.

Office Action, Final Rejection mailed on Apr. 20, 2001 for U.S. Appl. No. 09/155,152.

Office Action, Non-Final Rejection mailed on Nov. 4, 1999 for U.S. Appl. No. 09/210,671.

Office Action, Non-Final Rejection mailed on Aug. 7, 2002 for U.S. Appl. No. 09/966,515.

Office Action, Non-Final Rejection mailed on Nov. 19, 2002 for U.S. Appl. No. 09/966,515.

Office Action, Non-Final Rejection mailed on Dec. 4, 2002 for U.S. Appl. No. 10/013,868.

Office Action, Final Rejection mailed on May 20, 2003 for U.S. Appl. No. 10/013,868.

Office Action, Non-Final Rejection mailed on Oct. 25, 2002 for U.S. Appl. No. 10/013,294.

Office Action, Non-Final Rejection mailed on Aug. 30, 2005 for U.S. Appl. No. 10/201,382.

Office Action, Final Rejection mailed on Mar. 15, 2006 for U.S. Appl. No. 10/201,382.
Office Action, Non-Final Rejection mailed on Jan. 10, 2007 for U.S. Appl. No. 10/201,382.
Office Action, Final Rejection mailed on Sep. 10, 2007 for U.S. Appl. No. 10/201,382.
Office Action, Non-Final Rejection mailed on Nov. 16, 2005 for U.S. Appl. No. 10/288,935.
Office Action, Final Rejection mailed on Jun. 12, 2006 for U.S. Appl. No. 10/288,935.
Office Action, Non-Final Rejection mailed on Feb. 23, 2007 for U.S. Appl. No. 10/288,935.
Office Action, Final Rejection mailed on Oct. 4, 2007 for U.S. Appl. No. 10/288,935.
Office Action, Non-Final Rejection mailed on Aug. 24, 2006 for U.S. Appl. No. 10/658,873.
Office Action, Final Rejection mailed on Apr. 9, 2007 for U.S. Appl. No. 10/658,873.
Office Action, Non-Final Rejection mailed on Jan. 28, 2008 for U.S. Appl. No. 10/658,873.
Office Action, Final Rejection mailed on Jul. 10, 2008 for U.S. Appl. No. 10/658,873.
Office Action, Non-Final Rejection mailed on Dec. 15, 2006 for U.S. Appl. No. 10/684,633.
Office Action, Final Rejection mailed on Jun. 21, 2007 for U.S. Appl. No. 10/684,633.
Office Action, Non-Final Rejection mailed on Jan. 28, 2008 for U.S. Appl. No. 10/684,633.
Office Action, Non-Final Rejection mailed on May 3, 2007 for U.S. Appl. No. 10/912,367.
Office Action, Final Rejection mailed on Aug. 10, 2007 for U.S. Appl. No. 10/912,367.
Office Action, Non-Final Rejection mailed on Feb. 6, 2008 for U.S. Appl. No. 10/912,367.
Office Action, Final Rejection mailed on Dec. 1, 2008 for U.S. Appl. No. 10/912,367.
Office Action, Non-Final Rejection mailed on Apr. 2, 2008 for U.S. Appl. No. 11/216,858.
Office Action, Final Rejection mailed on Nov. 14, 2008 for U.S. Appl. No. 11/216,858.
Office Action, Non-Final Rejection mailed on Oct. 2, 2008 for U.S. Appl. No. 11/346,590.
Office Action, Non-Final Rejection mailed on Nov. 13, 2008 for U.S. Appl. No. 11/357,399.
Office Action, Non-Final Rejection mailed on Sep. 22, 2008 for U.S. Appl. No. 11/364,842.
Office Action, Non-Final Rejection mailed on Sep. 10, 2008 for U.S. Appl. No. 11/421,260.
Office Action, Non-Final Rejection mailed on Jan. 8, 2009 for U.S. Appl. No. 11/416,470.
Office Action, Non-Final Rejection mailed on Oct. 8, 2008 for U.S. Appl. No. 11/416,788.
Rajagopal et al. (1995), Int. J. Cancer 62: 661-667.
Dahiya et al. (1996), Urology 48: 963-970.
LeRiche et al. (1996), J. Clin. Endocrinol. Metab. 81: 656-662.
Pfeiffer et al. (1997), Int. J. Cancer 72: 581-586.
De Luca et al. (2000), Clin. Cancer Res. 6: 1439-1444.
Schlegel et al. (1994), Int. J. Cancer 56: 72-77.
Worm et al. (1999), Hum. Pathol. 30: 222-227.
Pawlowski et al. (2000), Cancer Detect. Prev. 24: 212-223.
Walch et al. (2001), Lab. Invest. 81: 791-801.
Sarkar et al. (1993), Diagn. Mol. Pathol. 2:210-218.
Gebhardt et al. (1998), Biochem. Biophys. Res. Comm. 247: 319-323.
Revillion et al. (1997), Clin. Chem. 43: 2114-2120.
Schneeberger et al. (1996), Anticancer Res. 16: 849-852.
Kraehn et al. (2001), Br. J. Cancer 84: 72-79.
Gamberi et al. (1998), Oncology 55: 556-563.
Sagawa et al. (2001), Cancer Letters 168: 45-50.
Christoph et al. (1999). Int. J. Cancer 84: 169-173.
Latil et al. (2000), Int. J. Cancer 89: 172-176.
Zhou et al. (1996), J. Biol. Chem. 271: 10760-10766.
Kozu et al. (1995), Genomics 25: 365-371.
Gocke et al. (2001), Clin. Chem. 47: 369, abstract 51.
Poon et al. (2001), Clin. Chem. 47: 363, abstract 11.
Urnovitz et al. (1999), Clin. Diag. Lab. Immunology 6: 330-335.
Zhao et al. (1994), Circulation 90: 677-685.
Dhillon et al. (2001), Exp. Neurol. 170:140-148.
Fleischhacker et al. (2001), Clin. Chem. 47: 369 (Oral Presentation).
El-Hefnawy et al. (2004), Clin. Chem. 50(3): 564-573.
Tschentscher et al. (2000), Int. J. Clin. Lab. Res. 30(1): 13-15.
Missov et al. (1999), Clinica Chimica Acta 284: 175-185.
Sarko et al. (2002), J. Emerg. Med. 23(1): 57-65.
Jurlander et al. (2000), Eur. Heart J. 21: 382-289.
Rainer et al. (2003), Clin. Chem. 50(1): 206-208.
Townsend et al. (1995), J. Mol. Cell. Cardiol. 27: 2223-2236.
Mizuno et al. (2001), Blood 97(5): 1172-1179.
Meikl et al. (1998), Leukemia 12: 311-316.
Eads et al. (1999), Cancer Res. 59: 2302-2306.
Robertson et al. (1999), Nucleic Acids Res. 27(11): 2291-2298.
Fleischhacker and Schmidt (2007), Biochim. Biophys. Acta 1775: 181-232.
Lion et al. (1995), Leukemia 9: 1353-1360.
El-Deiry, et al. (1991), Proc. Natl. Acad. Sci. U. S. A. 88: 3470-3474.
Lo et al. (1999), Clin. Chem. 45(8): 1292-1294.
Chen et al. (1999), Int. J. Cancer 83: 10-14.
Saito et al. (2001), Hepatology 33: 561-568.
Allouche et al. (1995), Leukemia 9(1): 77-86.
Garbarz et al. (1992), Blood 80(4): 1066-1073.
Guin et al. (1975), Biochemical Medicine 13(3): 224-230.
Kopreski et al. (1999), Clin. Cancer Res. 5: 1961-1965.
Kopreski et al. (2000), Ann. N. Y. Acad. Sci. 906: 124-128.
Leitzel et al. (1998), Clin. Cancer Res. 4: 3037-3043.
Tsui et al., "Stability of Endogenous and Added RNA in Blood Specimens, Serum, and Plasma," Clinical Chemistry 48 (10)1647-1653, 2002.
Serra et al. (2001), Neurological Sciences 22(2): 171-173.
Shen et al. (1995), Proc. Natl. Acad. Sci. U. S. A. 92: 6778-6782.
Shutack et al. (1968), J. Am. Osteopath. Assoc. 67(9): 1051-1053.
Stroun et al. (1978), Cancer Res. 38(10): 3546-3554.
Tamamiyagi et al. (1996), J. Dermatol. Sci. 11(2): 154-60.
Urdea et al. (1993), AIDS 7(suppl. 2): S11-S14.
Rohde et al. (2000), Clin. Cancer Res. 6: 4803-4809.
Keller et al. (1993), PCR Methods and Applications 3: 32-38.
Nolte et al. (1994), J. Clin. Microbiology 32: 519-520.
Schmidt et al. (1995), J. Med. Virology 47: 153-160.
Agliullina et al. (1988), Eksp. Onkol (USSR) 10(4), English abstract.
Schwarz et al. (1995), Res. Virol (Paris) 146(5), English abstract.
Kato et al. (1993), Hepatology 18(1), abstract.
Glick et al. (1994), Molecular biotechnology: Principles and applications of recombinant DNA, ASM Press: Washington DC. Table of Contents for Molecular Diagnostics (8) and Vaccines and Therapeutic Agents (9).
Persing et al (1993), Diagnostic molecular microbiology: Principles and applications, Amer. Soc. Microbiol. Washington DC, Table of Contents for Principles of Diagnostic Molecular Microbiology and Viral Pathogens.
Southall et al. (1990), Br. J. Cancer 61: 89-95.
Kopreski et al. (2001), Ann. N. Y. Acad. Sci 945: 172-178.
Yan-Sanders et al. (2002), Cancer Letters 183: 215-220.
Khimani et al. (2005), BioTechniques 38: 739-745.
Schrader et al. (2002), BMC Cancer 2: 32.
Fleischhacker et al. (2001), Ann. N. Y. Acad. Sci. 945: 179-188.
Burd et al. (1989), Proc. Natl. Acad. Sci. U. S. A. 86: 9788-9792.
Burchill et al. (1995), Br. J. Cancer 71: 278-281.
Lasheeb et al. (1997), Genitourinary Medicine 73(4): 303-305.
Mermin et al. (1991), J. Infectious Diseases 164(4): 769-772.
Kopreski et al. (2001), Clin. Chem. 47: 362, abstract 9.
Pelosi et al. (2006), Virchows Arch. 448: 7-15.
Tahara et al. (1999), Oncogene 18: 1561-1567.
Dasi et al. (2001), Lab. Investigation 81: 767-769.
Hasselmann et al. (2001), Oncol. Rep. 8: 115-118.
Ng et al. (2002), Clin. Chem. 48: 1212-1217.
Chen et al. (2000), Clin. Cancer Res. 6: 3823-3826.
Silva et al. (2001), Clin. Cancer Res. 7: 2821-2825.
Silva et al. (2001), Oncol. Rep. 8: 693-696.

Gal et al. (2001), Ann. N. Y. Acad. Sci. 945: 192-194.
Miura et al. (2003), Oncology 64: 430-434.
Wong et al. (2004), J. Clin. Pathol. 57: 766-768.
Ma et al. (2007), Haematologica 92: 170-175.
Arcari et al. (1984), Nucleic Acids Res. 12: 9179-9189.
Rykova et al. (2006), Ann. N. Y. Acad. Sci. 1075: 328-333.
Hernandez et al. (1999), Leukemia 13: 2087-2093.
Zhou et al. (1998), Clin. Cancer Res. 4: 1631-1640.
Zhou et al. (2001), Breast Cancer Research and Treatment 66: 217-224.
Press et al. (1990), Oncogene 5: 953-962.
Ng et al. (2003), Proc. Natl. Acad. Sci. U. S. A. 100: 4748-4753.

Ba Ray et al. (2002), Arch. Pathol. Lab. Med. 126: 574-576.
Gilmour et al. (2001), Cancer Res. 61: 2169-2716.
Reinhold et al. (2001), Clin. Chem. 47: 369, abstract 50.
Messner et al. (2000), Am. J. Clin. Pathol. 114(4): 544-549.
Monteyne et al. (1999), Acta Neurol. Belg. 99(1): 11-20.
Moreno et al. (1992), Cancer Res. 52: 5110-5112.
Wong et al., "Plasma RNA Integrity Analysis," Ann. N. Y. Acad. Sci. 1075:174-178 (2006).
Zhou et al., " Circulating RNA as a novel tumor marker: An in vitro study of the origins and characteristics of extracellular RNA," Cancer Letter 259:50-60 (2008).

* cited by examiner ically, the invention is directed towards methods for detecting
METHOD ENABLING USE OF EXTRACELLULAR RNA EXTRACTED FROM PLASMA OR SERUM TO DETECT, MONITOR OR EVALUATE CANCER This application claims priority for PCT/US97/03479, filed on Mar. 14, 1997, now WO 97/35589, and is a continuation of U.S. Ser. No. 09/966,515 filed on Sep. 28, 2001, now U.S. Pat. No. 6,759,217 B1, which is a continuation-in-part of U.S. Ser. No. 09/155,152, filed on Sep. 22, 1998, now U.S. Pat. No. 6,329,179 B1, the entire disclosure of U.S. Ser. No. 09/155,152 is hereby incorporated by reference.

BACKGROUND OF THE INVENTION

1. Field of the Invention

This invention relates to methods for detecting tumor-derived or tumor-associated mammalian ribonucleic acid (RNA) in bodily fluids such as blood plasma and serum obtained from an animal, most preferably a human. Specifically, the invention is directed towards methods for detecting RNA in bodily fluids from a human bearing a premalignant lesion or a malignancy, ranging in severity from localized neoplasia to metastatic disease. The methods of the invention are particularly drawn to detecting RNA encoding all or a portion of particular genes associated with neoplastic growth, development, or pathogenesis. In particular, these methods are drawn to genes associated with tumor growth factors such as tyrosine kinase mediated growth factors (for example, epidermal growth factor, EGF) and their receptors (for example, epidermal growth factor receptor (EGFr), and her-2/neu), as well as oncogenes such as c-myc oncogene. The methods of the invention are further particularly drawn to detecting RNA derived or associated with tumor-associated ribonucleoprotein, such as but not limited to heterogeneous nuclear ribonucleoprotein A2/B1 (hnRNP A2/B1) and associated ribonucleoprotein. In view of the essential role of RNA in expressing genes and producing proteins encoded thereby, detection and monitoring of RNA provides a convenient and reliable method for assessing and monitoring gene expression associated with neoplastic disease, thereby enabling the detection, diagnosis, monitoring, evaluation, and prognosticating of cancer and premalignancy.

2. Background of the Related Art

The pathogenesis and regulation of cancer is dependent upon gene expression, comprising production and translation of RNA to produce proteins involved with a variety of cellular processes, such as cell proliferation, regulation, and death. Furthermore, some gene expression, resulting in the existence of RNA and the proteins translated therefrom in cells and tissues, although not necessarily involved in neoplastic pathogenesis or regulation, may comprise a phenotype of recognizable characteristics for particular neoplasms, for example, either by being expressed at elevated levels or by being inappropriately expressed in said cells or tissues.

Tyrosine kinase-mediated growth factors and their receptors such as epidermal growth factor (EGF), epidermal growth factor receptor (EGFr), and her-2/neu, play important roles in the growth of many epithelial cancers and their response to insult or injury. Oncogenes such as c-myc play important roles in the pathogenesis of many cancers. Other proteins, such as hnRNP A2/B1 and associated ribonucleoproteins including hnRNP A2 (heterogeneous nuclear ribonucleoprotein A2) and hnRNP B1 (heterogeneous nuclear ribonucleoprotein B1) are overexpressed early in the development of some cancers. Detection of RNA encoding EGF, EGFr her-2/neu, c-myc or hnRNP A2/B1 provides a method for detecting and monitoring a wide spectrum of cancers and premalignancies, and can have prognostic significance. Tyrosine kinase-mediated growth factors and their receptors further provide potential targets for cancer therapies such as monoclonal antibody-based therapies (for example, herceptin for her-2/neu and CA-225 for EGFr), small molecule therapies and tyrosine kinase inhibitors, as well as vaccine therapies. Detection of EGF, EGFr and her-2/neu RNA can thus provide methods for selecting and monitoring patients for such therapies.

RNA associated with cancer and premalignant or neoplastic states, such as RNA encoding EGF, EGFr her-2/neu, c-myc or hnRNP A2/B1 are referred to herein as tumor-derived or tumor-associated RNA. Co-owned and co-pending U.S. patent application Ser. No. 09/155,152, incorporated by reference herein in its entirety, provides methods by which mammalian tumor-associated or tumor-derived RNA in bodily fluids such as plasma and serum can be detected and utilized for detecting, monitoring, or evaluating cancer or premalignant conditions. U.S. patent application Ser. No. 09/155,152, incorporated by reference herein in its entirety, further taught that tumor-associated or tumor-derived RNAs include erb-B-1 mRNA (also known as epidermal growth factor receptor mRNA), her-2/neu mRNA (also known as erb-B-2 mRNA), c-myc mRNA, and hnRNP A2/B1 associated RNA were advantageously detected in bodily fluids such as blood plasma or serum.

RNA encoding EGF, EGFr, her-2/neu, c-myc, and hnRNP A2/B1 being recognized as tumor-associated RNAs, there is a newly-appreciated need in the art to identify premalignant or malignant states characterized by said RNA in animals including humans by detecting said RNA in bodily fluids such as blood plasma or serum.

SUMMARY OF THE INVENTION

The present invention provides methods for detecting EGF RNA, EGFr RNA, her-2/neu RNA, and hnRNP A2/B1 RNA, or any combination thereof, in bodily fluids, preferably in blood and most preferably in blood plasma and serum, and in other bodily fluids including but not limited to urine, effusions, ascites, saliva, cerebrospinal fluid, cervical secretions, vaginal secretions, endometrial secretions, gastrointestinal secretions, sputum and bronchial secretions, and breast fluid and associated lavages and washings. The inventive methods comprise detecting extracellular mammalian tumor-associated or tumor-derived RNA such as EGF RNA, EGFr RNA, her-2/neu RNA c-myc RNA or hnRNP A2/B1 RNA, or any combination thereof, in said bodily fluids.

In preferred embodiments, the methods of the invention comprise the step of amplifying and detecting extracellular EGF RNA, EGFr RNA, her-2/neu RNA, c-myc RNA, and/or hnRNP A2/B1 RNA or any combination thereof from bodily fluids of an animal, most preferably a human.

In particularly preferred embodiments, the present invention provides methods for detecting EGF RNA, or EGFr RNA, or her-2/neu RNA, or c-myc RNA, or hnRNP A2/B1 RNA, or any combination thereof in blood or a blood fraction, including plasma and serum, and other bodily fluids. In these embodiments, the method comprises the steps of extracting mammalian RNA from blood, plasma, serum, or other bodily fluid, wherein a fraction of the extracted RNA comprises extracellular EGF RNA, EGFr RNA, her-2/neu RNA, c-myc RNA, or hnRNP A2/B1 RNA; or any combination thereof; in vitro amplifying RNA or cDNA corresponding thereto encoding EGF, EGFr, her-2/neu, c-myc, or hnRNP A2/B1 or any combination thereof; and detecting the amplified products produced from said mRNA or cDNA.

In a first aspect of this embodiment, the present invention provides methods for detecting EGF RNA, EGFr RNA, her-2/neu RNA, c-myc RNA, hnRNP A2/B1 or any combination thereof in blood or blood fractions, including plasma and serum, in an animal, most preferably a human. Said methods advantageously permit detection, diagnosis, monitoring, treatment, or evaluation of proliferative disorders, particularly stages of neoplastic disease, including premalignancy, early cancer, non-invasive cancer, carcinoma in-situ, invasive cancer, metastatic cancer and advanced cancer, as well as benign neoplasms. In this aspect, the method comprises the steps of extracting mammalian RNA from blood or blood plasma or serum, in vitro amplifying qualitatively or quantitatively a fraction of the extracted RNA or the corresponding cDNA wherein said fraction comprises EGF-, EGFr-, her-2/neu-, c-myc-, or hnRNP A1/A2-encoding RNA or combination thereof, and detecting the amplified products of said RNA or cDNA.

The invention in a second aspect provides methods for detecting EGF-, EGFr-, her-2/neu, -c-myc-, or hnRNP A2/B1-encoding RNA or any combination thereof in any bodily fluid. Preferably, said bodily fluid is whole blood, blood plasma, serum, urine, effusions, ascitic fluid, amniotic fluid, saliva, cerebrospinal fluid, cervical secretions, vaginal secretions, endometrial secretions, gastrointestinal secretions, bronchial secretions including sputum, secretions or washings from the breast, and other associated tissue washings from an animal, most preferably a human. In this aspect, the method comprises the steps of extracting mammalian RNA from the bodily fluid; in vitro amplifying in a qualitative or quantitative fashion a fraction of the extracted RNA, wherein said fraction comprises extracellular EGF RNA, EGFr RNA, her-2/neu RNA, c-myc RNA, hnRNP A2/B1 RNA or any combination thereof, or more preferably cDNA corresponding thereto, and detecting the amplified product of said RNA or cDNA.

In these embodiments, the inventive methods are particularly advantageous for detecting, diagnosing monitoring, treating, or evaluating proliferative disorders in an animal, most preferably a human, said proliferative disorders particularly including stages of neoplastic disease, including premalignancy, early cancer, non-invasive cancer, carcinoma-in-situ, invasive cancer, metastatic cancer and advanced cancer as well as benign neoplasm.

Thus, in another aspect the invention provides methods for evaluating an animal, most preferably a human, for premalignant or malignant states, disorders, or conditions. The inventive methods comprise detecting extracellular mammalian tumor-associated or tumor-derived RNA including EGF RNA, EGFr RNA, her-2/neu RNA c-myc RNA and hnRNP A2/B1 RNA or any combination thereof in bodily fluids, preferably blood and most preferably blood plasma and serum as well as in other bodily fluids, preferably urine, effusions, ascites, amniotic fluid, saliva, cerebrospinal fluid, cervical, vaginal, and endometrial secretions, gastrointestinal secretions, bronchial secretions, breast fluid, and associated tissue washings and lavages.

The methods of the invention are also useful for identifying EGF-, EGFr-, her-2/neu-, c-myc-, or hnRNP A2/B1-expressing cells or tissue in an animal, most preferably a human. In these embodiments, detection of an in vitro amplified product of EGF RNA, EGFr RNA, her-2/neu RNA, c-myc RNA, or hnRNP A2/B1 RNA or cDNA corresponding thereto using the methods of the invention indicates the existence of EGF, EGFr, her-2/neu, c-myc, or hnRNP A2/B1-expressing cells or tissue in a human.

The invention further provides diagnostic kits for detecting EGF RNA, EGFr RNA, her-2/neu RNA, c-myc RNA, hnRNPA2/B1 RNA or any combination thereof in bodily fluid, preferably blood plasma or serum, wherein the kit comprises oligonucleotide primers, probes, or both primers and probes for amplifying and detecting said EGF RNA, EGFr RNA, her-2/neu RNA, c-myc RNA, hnRNPA2/B1 RNA or any combination thereof or cDNA derived therefrom. In advantageous embodiments, the kit may further comprise instructions and reagents for performing methods for extracting RNA from the bodily fluid, reverse-transcribing said RNA into cDNA or reagents for performing in vitro amplification.

In preferred embodiments of the inventive methods, EGF RNA, EGFr RNA, her-2/neu RNA, c-myc RNA, hnRNP A2/B1 RNA or any combination thereof is extracted from whole blood, blood plasma or serum, or other bodily fluids using any effective extraction method including but not limited to gelatin extraction methods; silica, glass bead, or diatom extraction methods; guanidinium thiocyanate acid-phenol based extraction methods; guanidinium thiocyanate acid based extraction methods; methods using centrifugation through cesium chloride or similar gradients; phenol-chloroform based extraction methods; or other commercially available RNA extraction methods. In this aspect of the invention, RNA is extracted from plasma, serum, or other bodily fluid. In other aspects of the invention, extraction may alternatively be performed using probes that specifically hybridize to a particular RNA.

In preferred embodiments of the inventive methods, EGF RNA, EGFr RNA, her-2/neu RNA, c-myc RNA, hnRNP A2/B1 RNA or any combination thereof, or more preferably cDNA derived therefrom is amplified using an in vitro amplification method such as reverse transcriptase polymerase chain reaction (RT-PCR); ligase chain reaction; DNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; or any combination or variation thereof.

In preferred embodiments of the inventive methods, amplification products of EGF RNA, EGFr RNA, her-2/neu RNA, c-myc RNA, hnRNP A2/B1 RNA or any combination thereof, or more preferably cDNA produced therefrom, are detected using a detection method such as gel electrophoresis; capillary electrophoresis; conventional enzyme-linked immunosorbent assay (ELISA) or modifications thereof, such as amplification using biotinylated or otherwise modified primers; nucleic acid hybridization using specific labeled probes, such as fluorescent-, radioisotope-, or chromogenically-labeled probes; Southern blot analysis; Northern blot analysis; electrochemiluminescence; laser-induced fluorescence; reverse dot blot detection; and high-performance liquid chromatography.

In particularly preferred embodiments of the inventive methods, RNA is converted to cDNA using reverse transcriptase following extraction of RNA from a bodily fluid and prior to amplification.

The methods of the invention are advantageously used for providing a diagnosis of, or as a predictive indicator for determining risk for a human of developing a proliferative, premalignant, neoplastic, or malignant disease comprising or characterized by cells expressing EGF RNA, EGFr RNA, her-2/neu RNA, c-myc RNA, hnRNP A2/B1 RNA or any combination thereof.

The methods of the invention are particularly useful for providing a diagnosis of or for identifying in animals, particularly humans, who are at risk for developing or who have developed malignancy or premalignancy of cells comprising epithelial tissues. Most preferably, malignant or premalignant diseases, conditions, or disorders advantageously detected or diagnosed using the methods of the invention are diseases or disorders of breast, ovaries, lung, cervix, colorectal, stomach, pancreas, bladder, endometrium, kidney, head and neck, and esophageal cancers, and premalignancies and carcinoma in-situ such as bronchial dysplasia, atypical hyperplasia of the breast, ductal carcinoma in-situ, colorectal adenoma, atypical endometrial hyperplasia, and Barrett's esophagus.

In certain preferred embodiments of the methods of the invention, EGF RNA, EGFr RNA, her-2/neu RNA, c-myc RNA, hnRNP A2/B1 RNA or combinations thereof, or cDNA derived therefrom is amplified in a quantitative manner, thereby enabling quantitative comparison of said RNA present in a bodily fluid such as blood plasma or serum from a human. In these embodiments, the amount of extracellular EGF RNA, EGFr RNA, her-2/neu RNA, c-myc RNA, or hnRNP A2/B1 RNA or combinations thereof are detected in an individual and compared with a range of amounts of said extracellular RNA detected in the bodily fluid in a plurality of humans known to have a premalignant or malignant disease, or known to be free from a premalignant or malignant disease.

The invention further provides methods for identifying individuals having an EGF-, EGFr-, her-2/neu-, c-myc-, or hnRNP A2/B1-expressing malignancy or premalignancy, or a malignancy expressing any combination of said RNAs, thereby permitting rational, informed treatment options to be used for making therapeutic decisions. In particular, the methods of the invention are useful in identifying individuals having a premalignancy or malignancy that would benefit from a therapy directed at cells and tissues that express EGF, EGFr, her-2/neu-, c-myc-, or hnRNP 2/B1, such as monoclonal antibody therapy, anti-sense therapy, and vaccine therapy.

Another advantage of the use of the methods of the invention is that the methods can produce markers for assessing the adequacy of anticancer therapies such as surgical intervention, chemotherapy, biotherapy such as monoclonal antibody therapy or vaccines, anti-angiogenic therapy, and radiation therapy, and is also useful for determining whether additional or more advanced therapy is required. The invention therefore provides methods for developing a prognosis in such patients.

The methods of the invention also permit identification or analysis of EGF RNA, EGFr RNA, her-2/neu RNA, c-myc RNA, hnRNP A2/B1 RNA or any combination thereof, either qualitatively or quantitatively, in the blood or other bodily fluid of an animal, most preferably a human that has completed therapy, as an early indicator of relapsed cancer, impending relapse, or treatment failure.

Specific preferred embodiments of the present invention will become evident from the following more detailed description of certain preferred embodiments and the claims.

DETAILED DESCRIPTION OF THE PREFERRED EMBODIMENTS

The invention provides methods for detecting epidermal growth factor (EGF) RNA, epidermal growth factor receptor (EGFr) RNA, her-2/neu RNA, c-myc RNA, or heterogeneous nuclear ribonucleoprotein A2/B1 (hnRNP A2/B1) RNA, or any combination thereof in bodily fluids in an animal, most preferably a human. These methods are useful, inter alia, for detecting cancerous or precancerous cells in the animal.

In preferred embodiments of the methods of the invention, mammalian RNA in a bodily fluid, a portion thereof comprising extracellular EGF RNA, EGFr RNA, her-2/neu RNA, c-myc RNA hnRNP A2/B1 RNA, or any combination thereof is extracted from said bodily fluid. This extracted RNA is then amplified, either after conversion into cDNA or directly, using in vitro amplification methods in either a qualitative or quantitative manner, and using oligonucleotide primers specific for EGF RNA, EGFr RNA, her-2/neu RNA, c-myc RNA or hnRNP A2/B1 RNA or any combination thereof, or cDNA derived therefrom, to form a product DNA fragment having a size and sequence complexity specific for each of said specific RNAs. The amplified product is then detected in either a qualitative or a quantitative manner.

In the practice of the methods of the invention, mammalian RNA, a portion of which comprises extracellular EGF RNA, EGFr RNA, her-2/neu RNA, c-myc RNA, hnRNP A2/B1 RNA, or any combination thereof, is extracted from a bodily fluid, including but not limited to whole blood, plasma, serum, urine, effusions, ascitic fluid, saliva, cerebrospinal fluid, cervical secretions, vaginal secretions, endometrial secretions, amniotic fluid, gastrointestinal secretions, bronchial secretions including sputum, breast fluid or secretions or washings. Extraction can be performed using, for example, extraction methods described in co-owned and co-pending U.S. patent application Ser. No. 09/155,152, the entire disclosure of which is hereby incorporated by reference and include but are not limited to gelatin extraction methods; silica, glass bead, or diatom extraction methods; guanidinium thiocyanate acid-phenol based extraction methods; guanidinium thiocyanate acid based extraction methods; methods using centrifugation through cesium chloride or similar gradients; phenol-chloroform based extraction methods; or other commercially available RNA extraction methods. Alternatively, extraction may be performed using probes that specifically hybridize to a particular RNA, more preferably using isolation methods dependent thereupon, for example chromatographic methods and methods for capturing RNA hybridized to said specific primers. In a preferred embodiment, the bodily fluid is either blood plasma or serum. It is preferred, but not required, that blood be processed soon after drawing, and preferably within three hours, to minimize any degradation in the sample. In a preferred embodiment, blood is first collected by venipuncture and kept on ice until use. Preferably within 30 minutes of drawing the blood, serum is separated by centrifugation, for example at 1100×g for 10 minutes at 4 degrees centigrade. When using plasma, blood should not be permitted to coagulate prior to separation of the cellular and acellular blood components. Serum or plasma can be frozen, for example at −70 degrees centigrade after separation from the cellular portion of blood, until use. When using frozen blood plasma or serum, the frozen plasma or serum is rapidly thawed, for example in a water bath at 37 degrees centigrade, and RNA is extracted therefrom without undue delay, most preferably using a commercially available kit (for example the Perfect RNA Total RNA Isolation Kit obtained from Five Prime—Three Prime, Inc., Boulder, Colo.), according to the manufacturer's instructions. Other alternative and equivalent methods of RNA extraction are further provided in co-owned and co-pending U.S. patent application Ser. No. 09/155,152, incorporated herein by reference in its entirety.

Following extraction of RNA from a bodily fluid that contains EGF mRNA, EGFr mRNA, her-2/neu mRNA, c-myc mRNA, or hnRNP A2/B1 RNA, or any combination thereof, the EGF RNA, EGFr RNA, her-2/neu RNA, c-myc RNA, or hnRNP A2/B1 RNA or cDNA derived therefrom is amplified in vitro. Applicable amplification assays are detailed in co-owned and co-pending U.S. patent application Ser. No. 09/155,152, as herein incorporated by reference, and include but are not limited to reverse transcriptase polymerase chain reaction (RT-PCR), ligase chain reaction, DNA signal amplification, amplifiable RNA reporters, Q-beta replication, transcription-based amplification, boomerang DNA amplification, strand displacement activation, cycling probe technology, isothermal nucleic acid sequence based amplification, and other self-sustained sequence replication assays.

In preferred embodiments of the methods of the invention, RNA encoding EGF, EGFr, her-2/neu, c-myc, or hnRNP A2/B1, or any combination thereof is converted into cDNA using reverse transcriptase prior to in vitro amplification using methods known in the art. For example, a sample such as 10 microL extracted serum RNA is reverse-transcribed in a 30 microL volume containing 200 Units of Moloney murine leukemia virus (MMLV) reverse transcriptase (Promega, Madison, Wis.), a reaction buffer supplied by the manufacturer, 1 mM each dNTPs, 0.5 micrograms random hexamer oligonucleotide primers, and 25 Units of RNAsin (Promega, Madison, Wis.). Reverse transcription is typically performed under an overlaid mineral oil layer to inhibit evaporation, and incubated at room temperature for 10 minutes followed by incubation at 37 degrees C. for one hour. In another embodiment, reverse transcription is performed by the method of Rajagopal et al. (1995, Int. J. Cancer 62: 661-667), herein incorporated by reference in its entirety, or by the method of Dahiya et al. (1996, Urology 48: 963-970), herein incorporated by reference in its entirety.

Amplification oligonucleotide primers are selected to be specific for amplifying the nucleic acid of interest. In a preferred embodiment, amplification is performed by RT-PCR, wherein oligonucleotide primers are based upon gene or cDNA sequences using methods known to the art. In preferred embodiments, preferred oligonucleotide primers have nucleotide sequences as follows:

For epidermal growth factor (EGF) mRNA RT-PCR, the preferred primers are those as described by Rajagopal et al. (1995, Int. J. Cancer 62: 661-667), herein incorporated by reference in its entirety, wherein EGF primers (commercially available from Clonetech, Palo Alto, Calif.) have the sequence

```
5' TCTCAACACATGCTAGTGGCTGAAATCATGG
(5' Primer; SEQ ID No. 1)

5' TCAATATACATGCACACACCATCATGGAGC
(3' Primer; SEQ ID No. 2).
```

For EGF mRNA RT-PCR, other preferred primers are those as described by Dahiya et al. (1996, Urology 48: 963-970), herein incorporated by reference in its entirety, wherein primers for PCR of EGF cDNA have the sequence

```
5' TCTCAACACATGCTAGTGGCTGAAATCATGG
(Sense; SEQ ID No. 3)

5' TCAATATACATGCACACACCATCATGGAGGC
(Antisense; SEQ ID No. 4)
```

It is further to be understood that other primers for amplification of EGF cDNA or mRNA as determined using methods of the art are suitable for use in the invention, for example but not limitation primers described by LeRiche et al. (1996, J. Clin. Endocrinol. Metab. 81: 656-662), or Pfeiffer et al. (1997, Int. J. Cancer 72: 581-586), these references incorporated herein by reference in their entirety.

For epidermal growth factor receptor (EGFr) mRNA RT-PCR, the preferred primers are those described by De Luca et al. (2000, Clin. Cancer Res. 6: 1439-1444), herein incorporated by reference in its entirety, wherein primers for nested PCR of EGFr cDNA have the sequences:

```
Primer A: 5' TCTCAGCAACATGTCGATGG    (SEQ ID No. 5)

Primer B: 5' TCGCACTTCTTACACTTGCG    (SEQ ID No. 6)

Primer C: 5' TCACATCCATCTGGTACGTG    (SEQ ID No. 7)
```

It is further to be understood that other primers for amplification of EGFr cDNA or mRNA as determined using methods of the art are suitable for use in the invention, for example, primers described by LeRiche et al. (1996, J. Clin. Endocrinol. Metab. 81: 656-662) and by Dahiya et al. (1996, Urology 48: 963-970), these references herein incorporated by reference in their entirety. It is further to be understood that primers for amplification of altered, rearranged, deleted or splice mutated, or otherwise mutated EGFr gene mRNA or cDNA as determined using methods known to the art are suitable for use in the invention, whereby said mRNA is thereby detected in a bodily fluid, for example by using the primers as described by Schlegel et al. (1994, Int. J. Cancer 56: 72-77) or by Worm et al. (1999, Hum. Pathol. 30: 222-227), these references herein incorporated by reference in their entirety.

For her-2/neu mRNA RT-PCR, the preferred primers are those described Pawlowski et al. (2000, Cancer Detect. Prev. 24: 212-223), herein incorporated by reference in its entirety, wherein primers for conventional PCR of her-2/neu cDNA have the sequence:

```
5' GAGACGGAGCTGAGGAAGGTGAAG
(Sense; SEQ ID No. 8)

5' TTCCAGCAGGTCAGGGATCTCC
(Antisense; SEQ ID No. 9)
``` and wherein primers for real-time quantitative RT-PCR using a TaqMan fluorogenic probe (Perkin-Elmer) have the sequence:

```
5' CAACCAAGTGAGGCAGGTCC
(Sense; SEQ ID No. 10)

5' GGTCTCCATTGTCTAGCACGG
(Antisense; SEQ ID No. 11)

5' AGAGGCTGCGGATTGTGCGA
(TaqMan probe; SEQ ID No. 12)
``` wherein the TaqMan probe contains a 5' FAM (6-carboxyfluorescein) reporter dye and a 3' TAMRA (6-carboxy-tetramethyl-rhodamine) quencher dye and a 3' phosphate.

It is further understood that other primers for amplification of her-2/neu cDNA or mRNA are suitable for use as designed using methods known to the art, for example but not limitation primers described by Walch et al. (2001, Lab. Invest. 81: 791-801), Sarkar et al. (1993, Diagn. Mol. Pathol. 2: 210-218), Gebhardt et al. (1998, Biochem. Biophys. Res. Comm. 247: 319-323), Revillion et al. (1997, Clin. Chem. 43: 2114-

2120), or Schneeberger et al. (1996, *Anticancer Res.* 16: 849-852), these references incorporated herein by reference in their entirety.

For c-myc mRNA RT-PCR, the preferred primers are those described by Kraehn et al. (2001, *Br. J. Cancer* 84: 72-79), herein incorporated by reference in its entirety, wherein primers for PCR of c-myc cDNA are commercially available (Stratagene, Heidelberg, Germany), and have the sequence

```
5' CCAGCAGCGACTCTGAGG
(upstream primer; SEQ ID No. 13)

5' CCAAGACGTTGTGTGTTC
(downstream primer; SEQ ID No. 14)
```

It is further understood that other primers for qualitative or quantitative amplification of c-myc cDNA or mRNA are suitable for use as designed using methods known to the art, for example but not limitation primers described by Gamberi et al. (1998, *Oncology* 55: 556-563), Sagawa et al. (2001, *Cancer Letters* 168: 45-50), Christoph et al. (1999, *Int. J. Cancer* 84: 169-173), and Latil et al. (2000, *Int. J. Cancer* 89: 172-176), these references incorporated herein by reference in their entirety.

For hnRNP A2/B1 RNA RT-PCR, the preferred primers are those described by Zhou et al. (1996, *J. Biol. Chem.* 271: 10760-10766), herein incorporated by reference in its entirety, wherein primers for PCR of hnRNP A2/B1 associated cDNA have the sequence

```
5' GAGTCCGGTTCGTGTTCGTC    (SEQ ID No. 15)
5' TGGCAGCATCAACCTCAGC     (SEQ ID No. 16)
```

It is further understood that other primers for qualitative or quantitative amplification of hnRNP A2/B1 cDNA or RNA, or for amplification of associated RNA such as hnRNP A2 RNA or cDNA and hnRNP B1 RNA or cDNA, are suitable for use as designed using methods known to the art.

In one example of a preferred embodiment, RNA is harvested from approximately 1.75 mL aliquots of serum or plasma, and RNA extracted therefrom by the Perfect RNA Total RNA Isolation Kit (Five Prime—Three Prime, Inc., Boulder, Colo.) according to manufacturer's instructions. From this extracted RNA preparation, 10-20 microliters are reverse transcribed to cDNA as described above.

In a preferred embodiment, RT-PCR for EGF mRNA is performed by the method of Rajagopal et al. (1995, *Int. J. Cancer* 62: 661-667), incorporated herein by reference in its entirety, using 19 microliters of the EGF cDNA in a final volume of 100 microliters in a reaction mixture containing 2.5 U of AmpliTaq DNA Polymerase (Perkin Elmer Corp., Foster City, Calif.), 80 microliters of PCR buffer containing 10 mM Tris-HCl, pH 8.3, 50 mM KCl, 1.5 mM $MgCl_2$, 400 microM each dNTP, and 0.125 microM each of Primer SEQ ID No. 1 and Primer SEQ ID No. 2 identified above. The mixture is amplified in a single-stage reaction in a thermocycler under a temperature profile consisting of an initial 5 minute incubation at 94 degrees C., followed by 40 cycles of denaturation at 94 degrees C. for 10 seconds, annealing at 63 degrees C. for 30 seconds, and extension at 72 degrees C. for 30 seconds, followed by a final extension at 72 degrees C. for 10 minutes. Detection of the amplified product is achieved, for example by gel electrophoresis through a 3% Tris-borate-EDTA (TBE) agarose gel, using ethidium bromide staining for visualization and identification of the product fragment.

In alternative preferred embodiments, qualitative or quantitative amplification for EGF mRNA is performed by other methods known to the art, for example, methods as described by Dahiya et al. (1996, *Urology* 48: 963-970); LeRiche et al. (1996, *J. Clin. Endocrinol. Metab.* 81: 656-662); or Pfeiffer et al. (1997, *Int. J. Cancer* 72: 581-586), wherein these references are incorporated by reference herein in their entirety.

In a preferred embodiment, PCR amplification of EGFr cDNA is performed by the method of De Luca et al (2000, *Clin. Cancer Res.* 6: 1439-1444), herein incorporated by reference in its entirety. Eight microL of EGFr cDNA is used in a 25 microL reaction buffer containing 10 mM Tris-HCl, 1.5 mM $MgCl_2$, 50 mM KCl, 0.25 mM each dNTPs, 0.5 U Taq Gold polymerase (Perkin-Elmer), and 10 picomoles each of Primer A (SEQ ID No. 5, identified above) and Primer B (SEQ ID No. 6, identified above). The mixture is amplified in a two stage reaction in a thermocycler. In the first stage reaction, PCR is performed for 30 cycles under a temperature profile consisting of an initial 10 minute incubation at 94 degrees C., followed by 5 cycles of denaturation at 94 degrees C. for 30 seconds, annealing at 60 degrees C. for 45 seconds, and extension at 72 degrees C. for 45 seconds, followed by 25 cycles of denaturation at 94 degrees C. for 30 seconds, annealing at 55 degrees C. for 45 seconds, and extension at 72 degrees C. for 45 seconds, with the extension lengthened to 10 minutes during the last cycle. One microliter of the first stage product is then used for the second stage nested PCR in a mixture prepared as in the first stage except that the primers used are now Primer A (SEQ ID No. 5, identified above) and Primer C (SEQ ID No. 7, identified above). In the second stage reaction, nested PCR is performed for 35 cycles under a temperature profile consisting of an initial 10 minute incubation at 94 degrees C., followed by 5 cycles of denaturation at 94 degrees C. for 30 seconds, annealing at 60 degrees C. for 45 seconds, and extension at 72 degrees C. for 45 seconds, followed by 30 cycles of denaturation at 94 degrees C. for 30 seconds, annealing at 55 degrees C. for 45 seconds, and extension at 72 degrees C. for 45 seconds, with the extension lengthened to 10 minutes during the last cycle. The amplified product can then detected by gel electrophoresis through a 1.5% agarose gel with visualization by ethidium bromide staining. The amplified product can further be hybridized to an EGFr cDNA probe and visualized for example using streptavidin-alkaline phosphatase-coupled enhanced chemiluminescence (New England Biolabs, Beverly, Mass.).

In alternative preferred embodiments, qualitative or quantitative amplification for EGFr mRNA or cDNA, including EGFr mRNA or cDNA corresponding to a mutated or altered EGFr gene, is performed by methods known to the art, for example, methods described by LeRiche et al. 1996, *J. Clin. Endocrinol. Metab.* 81: 656-662), Dahiya et al (1996, *Urology* 48: 963-970), Schlegel et al. (1994, *Int. J. Cancer* 56: 72-77), and Worm et al. (1999, *Hum. Pathol.* 30: 222-227), these references herein incorporated by reference in their entirety.

In a preferred embodiment, PCR amplification of her-2/neu cDNA is performed by the method of Pawlowski et al. (2000, *Cancer Detection Prev.* 24: 212-223), herein incorporated by reference in its entirety, adapted as follows. A PCR reaction mixture is prepared in a 50 microL final volume containing 5 microL cDNA, 1.5 mM $MgCl_2$, 0.8 mM of each dNTP, 2 Units Taq DNA polymerase (Eurobio, Les Ulis, France), and 0.4 microM each her-2/neu primers (SEQ ID Nos. 8 and 9). PCR is performed in a thermocycler for 45 cycles under a temperature profile consisting of an initial denaturation at 94 degrees C. for 5 minutes, followed by denaturation at 94 degrees C. for 30 seconds, annealing at 60 degrees C. for 20 seconds, and extension at 72 degrees C. for 60 seconds, with a final extension at 72 degrees C. for 8 minutes. Detection of the amplified product is achieved, for example by gel electrophoresis through a 1.5% agarose gel, using ethidium bromide staining for visualization and identification of the product fragment.

In alternative preferred embodiments, qualitative or quantitative amplification for her-2/neu mRNA or cDNA is performed by other methods known to the art, for example, methods as described by Pawlowski et al. (2000, *Cancer Detection Prev.* 24: 212-223) for real-time quantitative RT-PCR, Walch et al. (2001, *Lab. Invest.* 81: 791-801), Sarkar et al. (1993, *Diagn Mol. Pathol.* 2: 210-218), Gebhardt et al. (1998, *Biochem. Biophys. Res. Comm.* 247: 319-323), Revillion et al. (1997, *Clin. Chem.* 43: 2114-2120), or Schneeberger et al. (1996, *Anticancer Res.* 16: 849-852), these references incorporated herein by reference in their entirety.

In a preferred embodiment, RT-PCR for c-myc mRNA is performed by the method of Kraehn et al. (2001, *Br. J. Cancer* 84: 72-79), incorporated herein by reference in its entirety, using 5 microliters of c-myc cDNA in a PCR reaction mixture containing PCR buffer, 1.5 mM $Mg^{2+}$, 0.2 mM each dNTP, 1.7 Units Taq polymerase (Boehringer, Mannheim, Germany), and 0.5 microM each c-myc primer (SEQ ID Nos. 13 and 14, identified above). The mixture is amplified in a thermocycler under a temperature profile consisting of an initial 4 minute denaturation at 94 degrees C., followed by 45 cycles of denaturation at 93 degrees C. for 35 seconds, annealing at 60 degrees C. for 35 seconds, and extension at 72 degrees C. for 35 seconds, followed by a final extension at 68 degrees C. for 10 minutes. Detection of the amplified product is achieved, for example by gel electrophoresis through a 2% agarose gel, using ethidium bromide staining for visualization and identification of the amplified product.

In alternative preferred embodiments, qualitative or quantitative amplification for c-myc mRNA or cDNA is performed by other methods known to the art, for example, methods described by Gamberi et al. (1998, *Oncology* 55: 556-563), Sagawa et al. (2001, *Cancer Letters* 168: 45-50), Christoph et al. (1999, *Int. J. Cancer* 84: 169-173), and Latil et al. (2000. *Int. J. Cancer* 89: 172-176), these references incorporated herein by reference in their entirety.

In a preferred embodiment, RT-PCR for hnRNP A2/B1 RNA is performed by the method of Zhou et al. (1996, *J. Biol. Chem.* 271: 10760-10766), incorporated herein by reference in its entirety, but wherein 5 microliters of cDNA is used in the reaction mixture, and the PCR amplification is performed for 45 cycles. The amplified product is then detected by gel electrophoresis through a 2% agarose gel using ethidium bromide staining for visualization and identification of the product. In alternative preferred embodiments, qualitative or quantitative amplification of hnRNP A2/B1 RNA, or associated RNA such as hnRNP A2 RNA or hnRNP B1 RNA is performed by other methods known to the art, for example, methods described by Kozu et al. (1995, *Genomics* 25: 365-371), incorporated by reference herein in its entirety.

In alternative preferred embodiments, amplified EGF, EGFr, her-2/neu, c-myc, or hnRNP A2/B1 RNA or any combination thereof or cDNA products thereof can be detected using methods, including but not limited to other gel electrophoresis methods; capillary electrophoresis; ELISA or modifications thereof, such as amplification using biotinylated or otherwise modified primers; nucleic acid hybridization using specific, detectably-labeled probes, such as fluorescent-, radioisotope-, or chromogenically-labeled probes; Southern blot analysis; Northern blot analysis; electrochemiluminescence; laser-induced fluorescence; reverse dot blot detection; and high-performance liquid chromatography. Furthermore, amplified product fragment detection may be performed in either a qualitative or quantitative fashion.

PCR product fragments produced using the methods of the invention can be further cloned into recombinant DNA replication vectors using standard techniques. RNA can be produced from cloned PCR products, and in some instances the RNA expressed thereby, for example, using the TnT Quick Coupled Transcription/Translation kit (Promega, Madison, Wis.) as directed by the manufacturer.

In another embodiment, restriction digestion may be performed upon a single-stage RT-PCR product. The products of the restriction digestion can be further amplified in a second stage amplification reaction using appropriate primers.

In a preferred embodiment, EGF, EGFr, her-2/neu, c-myc, or hnRNP A2/B1 RNA or any combination thereof or cDNA produced therefrom is amplified in a quantitative fashion thereby enabling comparison of the amount of said extracellular mRNA in an individual's bodily fluid with the range of amounts of said mRNA present in the bodily fluids of populations with cancer, premalignancy, or normal populations without cancer.

The methods of the invention as described above is not limited to blood plasma or serum, and can be performed in like manner for detecting extracellular EGF, EGFr, her-2/neu, c-myc, or hnRNP A2/B1 RNA or any combination thereof from other bodily fluids, including but not limited to whole blood, urine, effusions, ascitic fluid, saliva, cerebrospinal fluid, cervical secretions, vaginal secretions, endometrial secretions, amniotic fluid, gastrointestinal secretions, breast fluid or secretions, and bronchial secretions including sputum. Whereas fractionation of the bodily fluid into its cellular and non-cellular components is not required for the practice of the invention, the non-cellular fraction may be separated, for example, by centrifugation or filtration of the bodily fluid.

The methods of the invention are useful in the practice of diagnostic methods for detecting extracellular mRNA in an animal, most preferably a human at risk for developing or who has developed a premalignant or malignant neoplastic disease comprising cells expressing EGF, EGFr, her-2/neu, c-myc, or hnRNP A2/B1 RNA or any combination thereof. The invention further provides a method of identifying animals, particularly humans at risk for developing, or who have developed premalignancies or cancer of epithelial tissues and components of tissues, including but not limited to breast, ovarian, lung, cervical, colorectal, gastric, pancreatic, bladder, prostate, head and neck, endometrial, kidney, and esophageal cancers, as well as premalignancies and carcinoma in-situ including but not limited to cervical dysplasia and cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The diagnostic methods of the invention can be advantageously performed using a diagnostic kit as provided by the invention, wherein the kit includes oligonucleotide primers specific for cDNA synthesis of EGF, EGFr, her-2/neu, c-myc, or hnRNP A2/B1 RNA or any combination thereof, or in vitro amplification or both, or specific probes, most preferably oligonucleotide probes for detecting EGF, EGFr, her-2/neu, c-myc, or hnRNP A2/B1 RNA or associated hnRNP A2 or B1 RNA or any combination thereof or corresponding cDNA or in vitro amplified DNA fragments thereof. The kit can further include methods and reagents for extracting extracellular RNA from a bodily fluid, wherein the bodily fluid is most preferably but not limited to blood plasma or serum. The kit can further comprise reagents for reverse-transcribing said RNA into cDNA or reagents for performing in vitro amplification. The kit can further comprise instructions for performing methods for extracting RNA from the bodily fluid, reverse-transcribing said RNA into cDNA or for performing in vitro amplification.

The inventive methods have significant advantages in assigning and monitoring therapies not specifically directed at cells expressing EGF, EGFr, her-2/neu, c-myc, or hnRNP A2/B1 or any combination thereof, including chemotherapy, radiation therapy, and surgery. The inventive methods further have significant advantages in assigning and monitoring therapies directed at cells expressing EGF, EGFr, her-2/neu, c-myc, or hnRNP A2/B1 or any combination thereof, such as specific or directed therapies such as monoclonal antibody therapies directed at EGFr or her-2/neu, exemplified by Herceptin (Genentech), a her-2/neu-directed monoclonal antibody, and C225 (ImClone Systems), an EGFr-directed monoclonal antibody, or tyrosine kinase inhibitors and small molecule therapies, anti-sense therapies, and vaccine therapies. The methods of the invention permit stratification and selection of individuals, particularly individual human patients likely to benefit from these specific or directed therapies. The inventive methods are also useful for monitoring response, relapse, and prognosis of neoplastic disease associated with expression of EGF, EGFr, her-2/neu, c-myc, or hnRNP A2/B1 or any combination thereof. Of particular value, the invention allows a determination that a directed therapy is therapeutically indicated even in cases of premalignancy, early cancer, or occult cancers or minimum residual disease, as well as when metastatic disease is present. Thus, the invention permits therapeutic intervention when tumor burden is low, immunologic function is relatively intact, and the patient is not compromised, all increasing the potential for cure.

The methods of the invention further enable RNA encoding EGF, EGFr, her-2/neu, c-myc, or hnRNP A2/B1, or any combination thereof, to be evaluated in blood plasma, serum or other bodily fluid in combination with detection of other tumor-associated or tumor-derived RNA or DNA in a concurrent or sequential fashion, such as in a multiplexed assay or in a chip-based assay, thereby increasing the sensitivity or efficacy of the assay in the detection or monitoring of neoplastic disease. For example, EGF, EGFr, her-2/neu, c-myc, or hnRNP A2/B1 RNA, or any combination thereof can be detected in blood, plasma, serum, or other bodily fluid in combination with detection of telomerase-associated RNA such as hTR and/or hTERT, or in combination with detection of cancer-associated viral DNA such as human papillomavirus DNA, or in combination with oncogene DNA such as mutated K-ras DNA, or in combination with tumor suppressor gene DNA such as altered P53 or APC DNA and/or in combination with microsatellite DNA.

The methods of the invention and preferred uses for the methods of the invention are more fully illustrated in the following Examples. These Examples illustrate certain aspects of the above-described method and advantageous results. These Examples are shown by way of illustration and not by way of limitation.

Example 1

A 44 year old woman is diagnosed with metastatic breast cancer and seeks the recommendation of her physician regarding future treatment. The physician draws a peripheral blood specimen from the woman, and evaluates her plasma for the presence of her-2/neu RNA using the methods of the invention. Her-2/neu RNA is demonstrated in the woman's plasma, thereby selecting the woman for a her-2/neu directed therapy. The woman is treated with a monoclonal antibody that binds with the extracellular domain of her-2/neu, and additionally is treated with a cytotoxic chemotherapeutic agent such as a taxane that is known to be synergistic with the monoclonal antibody. The woman's response to therapy is consequently determined by serially monitoring in a quantitative fashion levels of her-2/neu RNA in the women's plasma or serum.

Example 2

A 56 year old man is being evaluated for his best treatment option after being diagnosed with colorectal cancer. Serum is obtained from the man's peripheral blood and is quantitatively evaluated for the level of EGFr RNA in the serum using the methods of the invention. It is thereby demonstrated that the man has higher levels of EGFr RNA in his blood than would be normally expected, and he is consequently treated with a monoclonal antibody that binds to the extracellular domain of the epidermal growth factor receptor. His response to therapy is monitored through serial determinations of the quantitative levels of EGFr RNA in his plasma or serum.

Example 3

A 60 year old man with a long history of smoking presents to his family physician with a complaint of increasing shortness of breath. The physician obtains a chest x-ray that demonstrates a large pleural effusion. The physician subsequently inserts a needle into the pleural space thereby aspirating pleural fluid, which he further evaluates for the presence of tumor cells and for extracellular tumor-associated RNA. Cytology is performed on the fluid but no tumor cells are diagnosed. The fluid is further centrifuged, and the non-cellular component of the pleural fluid is analyzed in multiplexed fashion using the methods of the invention for extracellular her-2/neu RNA, hnRNP A2/B1 RNA, c-myc RNA, and additionally the telomerase RNA hTERT and mutant K-ras DNA. The pleural fluid demonstrates the presence of her-2/neu RNA, hnRNP A2/B1 RNA, and hTERT RNA. The presence of said RNA in the man's pleural fluid strongly supports the diagnosis of a neoplastic disease of the lung. The man subsequently undergoes further radiologic evaluation including magnetic resonance imaging (MRI) and bronchoscopy with biopsy, thereby confirming the diagnosis of lung cancer. The man is treated by surgical resection, followed by treatment with a her-2/neu directed monoclonal antibody in combination with cytotoxic chemotherapy and radiotherapy.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

I claim:

1. A method for detecting heterogeneous nuclear ribonucleoprotein A2/B1 RNA in blood plasma from a human, the method comprising the steps of:
   a) centrifuging blood from a human and obtaining blood plasma;
   b) extracting extracellular total RNA from said blood plasma from said human and obtaining the extracellular total RNA;
   c) amplifying a fraction of the extracellular total RNA or cDNA prepared therefrom, either qualitatively or quantitatively, using primers specific for heterogeneous nuclear ribonucleoprotein A2/B1 RNA, or cDNA therefrom, and producing an amplified product; and
   d) assaying either quantitatively or qualitatively the amplified product to detect heterogeneous ribonucleoprotein A2/B1 RNA in the blood plasma.

2. A method for detecting heterogeneous nuclear ribonucleoprotein A2/B1 RNA in blood serum from a human, the method comprising the steps of:
   a) extracting extracellular total RNA from blood serum of a human and obtaining the extracellular total RNA;
   b) amplifying a fraction of the extracellular total RNA or cDNA prepared therefrom, either qualitatively or quantitatively, using primers specific for heterogeneous nuclear ribonucleoprotein A2/B1RNA, or cDNA therefrom, and producing an amplified product; and
   c) assaying either quantitatively or qualitatively the amplified product to detect heterogeneous ribonucleoprotein A2/B1 RNA in the blood serum.

3. A method for detecting heterogeneous nuclear ribonucleoprotein A2/B1 RNA in pleural fluid from a human, the method comprising the steps of:
   a) extracting extracellular total RNA from pleural fluid from a human and obtaining the extracellular total RNA;
   b) amplifying a fraction of the extracellular total RNA or cDNA prepared therefrom, either qualitatively or quantitatively, using primers specific for heterogeneous nuclear ribonucleoprotein A2/B1RNA, or cDNA therefrom, and producing an amplified product; and
   c) assaying either quantitatively or qualitatively the amplified product to detect heterogeneous ribonucleoprotein A2/B1 RNA in the pleural fluid.

* * * * *

SEQUENCE LISTING

<160> NUMBER OF SEQ ID NOS: 15

<210> SEQ ID NO 1
<211> LENGTH: 31
<212> TYPE: DNA
<213> ORGANISM: Homo sapiens

<400> SEQUENCE: 1
tctcaacaca tgctagtggc tgaaatcatg g                          31

<210> SEQ ID NO 2
<211> LENGTH: 31
<212> TYPE: DNA
<213> ORGANISM: Homo sapiens

<400> SEQUENCE: 2
tcaatataca tgcacacacc atcatggagg c                          31

<210> SEQ ID NO 3
<211> LENGTH: 31
<212> TYPE: DNA
<213> ORGANISM: Homo sapiens

<400> SEQUENCE: 3
tcaatataca tgcacacacc atcatggagg c                          31

<210> SEQ ID NO 4
<211> LENGTH: 20
<212> TYPE: DNA
<213> ORGANISM: Homo sapiens

<400> SEQUENCE: 4
tctcagcaac atgtcgatgg                                       20

<210> SEQ ID NO 5
<211> LENGTH: 20
<212> TYPE: DNA
<213> ORGANISM: Homo sapiens

<400> SEQUENCE: 5
tcgcacttct tacacttgcg                                       20

<210> SEQ ID NO 6
<211> LENGTH: 20
<212> TYPE: DNA
<213> ORGANISM: Homo sapiens

<400> SEQUENCE: 6
tcacatccat ctggtacgtg                                       20

<210> SEQ ID NO 7
<211> LENGTH: 24
<212> TYPE: DNA
<213> ORGANISM: Homo sapiens

<400> SEQUENCE: 7
gagacggagc tgaggaaggt gaag                                  24

<210> SEQ ID NO 8
<211> LENGTH: 22
<212> TYPE: DNA
<213> ORGANISM: Homo sapiens

```
<400> SEQUENCE: 8
ttccagcagg tcagggatct cc                                          22

<210> SEQ ID NO 9
<211> LENGTH: 20
<212> TYPE: DNA
<213> ORGANISM: Homo sapiens

<400> SEQUENCE: 9
caaccaagtg aggcaggtcc                                             20

<210> SEQ ID NO 10
<211> LENGTH: 21
<212> TYPE: DNA
<213> ORGANISM: Homo sapiens

<400> SEQUENCE: 10
ggtctccatt gtctagcacg g                                           21

<210> SEQ ID NO 11
<211> LENGTH: 20
<212> TYPE: DNA
<213> ORGANISM: Homo sapiens

<400> SEQUENCE: 11
agaggctgcg gattgtgcga                                             20

<210> SEQ ID NO 12
<211> LENGTH: 18
<212> TYPE: DNA
<213> ORGANISM: Homo sapiens

<400> SEQUENCE: 12
ccagcagcga ctctgagg                                               18

<210> SEQ ID NO 13
<211> LENGTH: 18
<212> TYPE: DNA
<213> ORGANISM: Homo sapiens

<400> SEQUENCE: 13
ccaagacgtt gtgtgttc                                               18

<210> SEQ ID NO 14
<211> LENGTH: 20
<212> TYPE: DNA
<213> ORGANISM: Homo sapiens

<400> SEQUENCE: 14
gagtccggtt cgtgttcgtc                                             20

<210> SEQ ID NO 15
<211> LENGTH: 19
<212> TYPE: DNA
<213> ORGANISM: Homo sapiens

<400> SEQUENCE: 15
tggcagcatc aacctcagc                                              19
```